United States Patent
Simonton et al.

(10) Patent No.: US 9,259,507 B2
(45) Date of Patent: Feb. 16, 2016

(54) TISSUE AUGMENTATION WITH ACTIVE AGENT FOR WOUND HEALING

(75) Inventors: Thomas Andrew Simonton, Memphis, TN (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 976 days.

(21) Appl. No.: 12/427,087

(22) Filed: Apr. 21, 2009

(65) Prior Publication Data

US 2010/0266689 A1    Oct. 21, 2010

(51) Int. Cl.
*A61K 9/14*    (2006.01)
*A61L 26/00*    (2006.01)

(52) U.S. Cl.
CPC ........... *A61L 26/009* (2013.01); *A61L 26/0066* (2013.01); *A61L 26/0085* (2013.01); *A61L 26/0095* (2013.01); *A61L 2300/414* (2013.01); *A61L 2300/426* (2013.01); *A61L 2300/64* (2013.01)

(58) Field of Classification Search
CPC ............. A61K 9/00; A61K 9/06; A61K 9/14; A61K 47/00; A61K 47/48007; A61K 47/48784; A61K 2300/00; A61K 2800/95
See application file for complete search history.

(56) References Cited

U.S. PATENT DOCUMENTS

| | | | | |
|---|---|---|---|---|
| 4,285,987 A | * | 8/1981 | Ayer et al. .................... 427/2.16 |
| 4,618,490 A | | 10/1986 | De Marco | |
| 4,808,353 A | * | 2/1989 | Nambu et al. ................... 264/28 |
| 5,128,326 A | * | 7/1992 | Balazs et al. ..................... 514/54 |
| 5,529,914 A | * | 6/1996 | Hubbell et al. ............... 435/182 |
| 5,846,530 A | * | 12/1998 | Soon-Shiong et al. ...... 424/93.7 |
| 6,132,759 A | | 10/2000 | Schacht et al. | |
| 6,165,488 A | | 12/2000 | Tardy et al. | |
| 6,287,588 B1 | | 9/2001 | Shih et al. | |
| 6,863,899 B2 | | 3/2005 | Koblish et al. | |
| 7,052,497 B2 | | 5/2006 | Sherman et al. | |
| 7,749,267 B2 | * | 7/2010 | Karmon .................... 623/16.11 |
| 7,897,164 B2 | * | 3/2011 | Scifert .......................... 424/422 |
| 2002/0048601 A1 | * | 4/2002 | Beckett et al. ................ 424/486 |
| 2005/0042288 A1 | | 2/2005 | Koblish et al. | |
| 2005/0267577 A1 | | 12/2005 | Trieu | |
| 2006/0189986 A1 | | 8/2006 | Sherman et al. | |
| 2007/0213822 A1 | | 9/2007 | Trieu | |
| 2007/0213823 A1 | | 9/2007 | Trieu | |

OTHER PUBLICATIONS

Bourke et al. AAPS PharmSci 2003;5:article 33, pp. 1-11.*
Chiellini et al. Prog Polym Sci 2003;28:963-1014.*
Bryant et al. ISA 1999;Paper#99-053, pp. 309-314.*
Balakrishnan et al. Biomaterials 2005;26:6335-42.*
Bourke et al. AAPS PharmSci 2003;5:E33.*
Allen et al. Spine 2004;29:515-23.*
Budai et al. Intl J Pharmaceutics 2007;343:34-40.*

* cited by examiner

*Primary Examiner* — Janice Li
(74) *Attorney, Agent, or Firm* — Sorrell Lenna & Schmidt LLP

(57) ABSTRACT

The invention relates to a bioactive settable hydrogel matrix having a pore creating material, which may also carry a therapeutic agent, and methods of using the same, for example, use in promoting internal wound healing, tissue repair, tissue regeneration.

13 Claims, No Drawings

TISSUE AUGMENTATION WITH ACTIVE AGENT FOR WOUND HEALING

The present invention relates to a bioactive settable hydrophilic polymer and methods of using the same.

BACKGROUND

Any publications or references discussed herein are presented to describe the background of the invention and to provide additional detail regarding its practice. Nothing herein is to be construed as an admission that the inventors are not entitled to antedate such disclosure by virtue of prior invention.

The replacement or repair of damaged or diseased tissues or organs by implantation is a continuing goal of the medical profession. As a part of that work, there is an increasing interest in tissue engineering techniques where biocompatible, biodegradable materials are used as a support matrix or as a substrate for the delivery of therapeutic agents. However, there are a number of difficulties that restrict the use of implanted materials.

One particular class of polymers that have proven useful are hydrogels. Hydrogels are materials consisting of a three-dimensional network of hydrophilic polymers with water filling the space between the polymer chains. Hydrogels may be obtained by copolymerizing suitable hydrophilic monomers, by chain extension, and by cross-linking hydrophilic pre-polymers or polymers.

A thermoreversible hydrogel matrix, which is liquid near physiologic temperatures, has been shown to elicit vasculogenesis and modulate wound healing. This bioactive hydrogel material has also been shown to improve healing in response to implanted foreign materials; demonstrating a decrease in the surrounding fibrous capsule thickness and a persistent increase in blood supply immediately adjacent to implanted materials exposed to this thermoreversible hydrogel. However, that thermoreversible hydrogel is molten at physiologic temperatures, rendering it inappropriate for use in vivo (see WO 2003/072155).

A particular biopolymer for use in medical applications is disclosed in U.S. Pat. No. 6,132,759, which relates to a biopolymer matrix comprising gelatin cross-linked with oxidized polysaccharides. The biopolymer of the '759 patent is said to be useful for treating skin wounds or dermatological disorders when appropriate drugs are incorporated.

U.S. Pat. No. 5,972,385 describes a matrix comprising a modified polysaccharide with collagen for tissue repair, which can be combined with growth factors.

U.S. Pat. No. 6,287,588 describes a matrix comprising a continuous biocompatible gel phase, such as a hydrogel, and a discontinuous particulate phase, such as microspheres, and a therapeutic agent contained in both phases. The '588 patent does not discuss wound sealing or any use in conjunction with an interbody device.

Additional publications and patents have described polymers and co-polymers for use in medical applications, such as drug delivery, tissue regeneration, wound healing, wound dressings, adhesion barriers, and wound adhesives. For example, see U.S. Pat. No. 4,618,490 and U.S. Pat. No. 6,165,488.

A large number of the biocompatible polymers previously known are based at least in part on collagen, collagen derived material, polysaccharides, particularly dextran and cross-linked gelatin and dextran.

In addition, wound sealants known in the art typically rely upon the use of fibrinogen, thromboplastin and/or a clotting factor, for example, see WO 97297972, U.S. Pat. No. 5,219,328, U.S. Pat. No. 5,292,333, U.S. Pat. No. 5,645,849, U.S. Pat. No. 5,643,596, U.S. Pat. No. 6,168,788, U.S. Pat. No. 5,981,621, and U.S. Pat. No. 6,607,631.

In addition, there still remains a need for a hydrogel that is settable when in contact with living tissue and that functions as a wound sealant that fosters tissue growth, and that optionally can effectively deliver a therapeutic agent.

SUMMARY OF THE INVENTION

The invention relates to a bioactive settable hydrogel matrix having a pore creating material, which may also carry a therapeutic agent, and methods of using the same, for example, use in promoting internal wound healing, tissue repair, and/or tissue regeneration.

In one aspect, the invention provides compositions and methods for a sustained release of a therapeutic agent. Such compositions may comprise a biologically absorbable hydrophilic polymer and a pore creating material dispersed discontinuously within the biologically absorbable hydrophilic polymer, wherein the pore creating material carries a therapeutic compound that is released upon absorption or degradation of the pore creating material. Such a composition may be used to treat an internal wound site, by sealing the wound area, delivering a therapeutic agent to the wound as the pore creating material is absorbed or degraded, and where the pores are useful in facilitating colonization of the polymer by appropriate cells, which can then degrade or absorb the hydrophilic polymer as healing progresses.

The biologically absorbable hydrophilic polymer in its cross-linked state may have at least one of the following properties, swelling of less than about 10% by volume, strong adhesion to biological tissue, a burst strength of at least about 3 psi, and/or a residence time of at least about 4 weeks in the patient before the hydrophilic polymer is fully absorbed or degraded. In another exemplary embodiment, the biologically absorbable hydrophilic polymer in its cross-linked state may have a burst strength of at least about 2 psi, about 2.5 psi or about 3 psi. The biologically absorbable hydrophilic polymer in its cross-linked state may swell less than about 15%, less than about 13%, less than about 11%, less than about 9%, or less than about 7%.

In an exemplary embodiment, the biologically absorbable hydrophilic polymer sets to form a cross-linked polymer that forms a liquid barrier covering the wound. The polymer may transition from the non-cross-linked state to a fully cross-linked state in less than 10 minutes, less than 9 min., less than 8 min., less than 7 min., less than 6 min., less than 5 min., less than 4 min., less than 3 min., less than 2 min., less than 1 min., less than 30 seconds, less than 15 seconds, less than 10 seconds, less than 5 seconds, less than 4 seconds, less than 3 seconds, less than 2 seconds or less than 1 second after application of the cross-linking agent to the polymer and wound surface. The pore creating material is gradually removed from the biologically absorbable hydrophilic polymer in vivo creating a porous scaffold that supports in growth of cells, either existing in situ or delivered separately. In exemplary embodiments, the rate of absorption of the pore creating material from the hydrophilic polymer is faster than the rate of absorption of the biologically absorbable hydrophilic polymer.

In an exemplary embodiment the invention provides the use of a biologically absorbable hydrophilic polymer and a pore creating having a therapeutic agent within the pore creating material.

In an exemplary embodiment, the hydrophilic polymer is polymerized or cross-linked without using irradiation, light or heat, in addition, the composition may exclude doxycycline, thrombin, fibrinogen, collagen, gelatin and/or a polysaccharide, and/or have the therapeutic agent substantially absent from the hydrophilic polymer and contained entirely in the pore creating material, and/or completely lacking a fabric support.

The therapeutic agent may promote tissue regeneration and/or healing. Suitable therapeutic agents include, but are not limited to, Vascular Endothelial Growth Factors (VEGFs), Connective Tissue Growth Factors (CTGFs), Platelet Derived Growth Factors (PDGFs), insulin-related growth factor-I (IGF-I), insulin-related growth factor-II (IGF-II); fibroblast growth factor (FGF), beta-2-microglobulin (BDGF II), Bone Morphogenetic Proteins (BMPs, e.g., BMP-2, BMP-7, BMP-12 and/or GDF-5), Transforming Growth Factor betas (TGF-βs) or combinations thereof. The one or more therapeutic agents are released from the pore creating material as the pore creating material is being removed from the biologically absorbable hydrophilic polymer.

In an exemplary embodiment, the hydrophilic polymer comprises poly vinyl alcohol (PVA) and copolymers thereof. In another exemplary embodiment, the hydrophilic polymer is cross-linked using free radical polymerization that is redox initiated.

The invention also relates to the manufacture of a medicament for the treatment of an internal wound. The invention also relates to a kit comprising a first container comprising a hydrophilic polymer and a second a container comprising a cross-linking agent, wherein combining the contents of the first container with the contents of the second container initiates polymerization or cross-linking to produce a sealant over the wound. Optionally, the kit may contain a third container comprising a therapeutic agent.

DETAILED DESCRIPTION OF THE INVENTION

For the purposes of promoting an understanding of the principles of the invention, reference will now be made to certain embodiments and specific language will be used to describe the same. Nevertheless, it will be understood that no limitation of the scope of the invention is intended by the reference to the embodiments and that alterations and further modifications of the illustrated device, along with further applications of the principles of the invention described herein, will be recognized in light of the present disclosure by one skilled in the art to which the invention relates.

The uses of the terms "a" and "an" and "the" and similar references in the context of describing the invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each separate value in the range is incorporated into the specification as if it were individually recited herein.

All methods described herein may be performed in any suitable order unless otherwise indicated or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element is essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein, the term "to seal" or "sealing" refers to the act wherein a hole, tear, cut, perforation or other discontinuity in a tissue or tissue junction is covered by the material of the invention and requires at least some degree of adhesion of the material to the tissue around the hole, tear, cut, perforation or other discontinuity to which it is applied.

The discontinuity in the tissue that is being sealed may be an incision made as part of a surgical procedure, or it may be a wound.

As used herein, the "sealant" is the material which is used to seal a hole, tear, cut, perforation or other discontinuity in a tissue or tissue junction comprising a biologically absorbable hydrophilic polymer. The sealant, at least to some degree, adheres to the surrounding tissue, such that the sealant material is resistant to detachment.

The "biologically absorbable hydrophilic polymer" or "hydrophilic polymer" means a water absorbing polymer that, when applied to an internal wound, sets to provide a protective covering over the wound. Because the hydrophilic polymer will replace or augment the natural tissue that usually seals the particular organ or structure until the wound is healed, the hydrophilic polymer preferably possesses similar properties to the natural tissue. For example, the hydrophilic polymer is formulated such that the formed implant has sufficient elasticity, adhesiveness and a rapid setting time (e.g., less than about 2 minutes). In addition, the material preferably possess such qualities as mechanical strength, promotion of tissue formation, biodegradability, biocompatibility, sterilizability, optimum curing temperature, and good bonding strength to help seal an internal wound site. In an exemplary embodiment, the biologically absorbable hydrophilic polymer sets up, or partially sets up, upon delivery. Preparation of in-situ curable materials is known in the art and is disclosed, for example, in U.S. Pat. Nos. 6,703,041, 6,287, 588, 6,312,725, 7,070,809 and 7,135,140.

One advantage of the present invention is the ability of a tissue sealant made of a hydrophilic polymer to exchange nutrients and small molecules across the barrier while preventing blood loss and invasion of unwanted cells, e.g., bacterial. Prior art tissue sealants utilizing hydrophobic polymers will be unable to exchange water soluble nutrients, which prevents or hinders their use for internal wounds where nutrient supply may very well need to cross the tissue sealant barrier.

In an exemplary embodiment, the invention utilizes a hydrophilic polymer comprising biodegradable block copolymers that form solutions at lower temperatures and transition to a gel state when at or above the gelation temperature, preferably at about 28° C. to about 37° C.

A wide variety of biocompatible hydrophilic polymeric materials may be used, including, but are not limited to, silicon, polyurethane, copolymers of silicon and polyurethane, polyolefins, such as polyisobutylene and polyisoprene, neoprene, nitrile, polyvinyl alcohol, acrylamides such as polyacrylic acid and poly(acrylonitrile-acrylic acid), non-biologically absorbable polyurethanes, polyethylene glycol, poly(N-vinyl-2-pyrrolidone), acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, glycosaminoglycans, polyethylene oxide, co-polymers of PVA and PVP, and combinations thereof. The hydrogel materials may further be cross-linked to provide further strength. Examples of polyurethanes include thermoplastic polyurethanes, aliphatic polyurethanes, segmented polyurethanes, hydrophilic polyurethanes, polyether-urethane, polycarbonate-urethane and silicon polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, and combinations thereof.

Other suitable examples of the biologically absorbable hydrophilic polymers include biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. One can also use superabsorbent polymers (SAP) with or without additives. Superabsorbent polymers may include polymer chains that are synthetic, natural, and hybrid synthetic/natural polymers. Exemplary superabsorbent polymers may include, but are not limited to, polyacrylic acid, polymethacrylic acid, polymaleic acid, copolymers thereof, and alkali metal and ammonium salts thereof; graft copolymers of starch and acrylic acid, starch and saponified acrylonitrile, starch and saponified ethyl acrylate, and acrylate-vinyl acetate copolymers saponified; polyvinylpyrrolidone, polyvinyl alkylether, polyethylene oxide, polyacrylamide, and copolymers thereof; copolymers of maleic anhydride and alkyl vinylethers; saponified starch graft copolymers of acrylonitrile, acrylate esters, vinyl acetate, and starch graft copolymers of acrylic acid, methyacrylic acid, and maleic acid; the product of crosslinking acrylamide with backbones of kappa-carrageenan and sodium alginate using methylenebisacrylamide and potassium persulfate; and the product of crosslinking, using a bifunctional crosslinking reagent, an acyl-modified protein matrix such as soy protein isolate which has been acyl-modified by treatment with ethylenediaminetetraacetic acid dianhydride; mixtures and combinations thereof. Further, one can use silicon-based materials, polyethylene terephthalate, polycarbonate, thermoplastic elastomers and copolymers such as etherketone polymers such as poly etheretherketone.

Crosslinking of the polymer subunits may be done by any method known in the art, including, but not limited to, physical crosslinking such as hydrogen bonding and ionic bonding and chemical crosslinking such as chain addition polymerization, condensation polymerization, free radical polymerization and other methods of increasing the molecular weight of polymers/oligomers to very high molecular weights. See U.S. Patent Pub. 20050129656.

The term "pore creating material" means a substance that is dispersed within the biologically absorbable hydrophilic polymer prior to delivery into a patient and that creates a porous structure when removed (e.g., absorbed or degraded) from the biologically absorbable hydrophilic polymer. In the instant compositions, the initial ratio of the biologically absorbable hydrophilic polymer to the pore creating material may be between about 5% and about 95%, between about 15% and about 85%, or between about 25% and about 75%, wherein removal of the pore creating material from the biologically absorbable hydrophilic polymer creates pores of between about 100 μm and about 400 μm or between about 250 μm and about 350 μm.

The hydrophilic polymer of the invention may be resorbed over about 2 weeks to about 12 weeks, and more preferably over about 4 weeks to about 8 weeks, and most preferably over about 4 weeks to about 6 weeks.

In the context of this application, the pore creating material is removed from the biologically absorbable hydrophilic polymer in vivo, after the composition is applied to the patient. The term "removed" means gradual removal by resorbtion, resorption, dissolution, bursting, disintegration, degradation and so forth. The pore creating material may be removed from the biologically absorbable hydrophilic polymer over a period of time between about one to about two weeks, about 4 days to about 10 days, about 12 hours and about 96 hours, between about 24 hours and about 72 hours, or between about 24 hours and about 48 hours. Removal of the pore creating material from the biologically absorbable hydrophilic polymer, creates pores in the range of about 50 microns to about 400 microns, and optionally releases a therapeutic agent.

In some embodiments, the pore creating material may comprise microparticles or nanoparticles, such as spheres, rods, pellets, beads, and so forth, made from biologically absorbable materials. In preferred embodiments, the pore creating material is provided as microspheres with a diameter between about 50 microns to 400 microns, between about 100 microns and about 300 microns, or between about 100 microns and about 200 microns. In another exemplary embodiment, the pore creating material is present at a sufficient concentration or density so as to create interconnected pores or channels through the biologically absorbable hydrophilic polymer material.

Many of the materials suitable for use as biologically absorbable hydrophilic polymers are also suitable for use as microparticles or nanoparticles. Again, if the hydrophilic polymer is the same chemical structure as the pore creating material, the pore creating material is formulated such that the rate of removal of the pore creating material from the hydrophilic polymer is faster than the rate that the hydrophilic polymer is removed from the patient's body. For example, the hydrophilic polymer may be modified, such as by crosslinking, to ensure that its stays in the body for longer period of time, in which case the pore creating material would not be cross-linked or would have less cross-linking such that it is removed faster. For example, a pore creating material may be a microparticle made of hydrogels, fast resorbing cements or ceramics, hyaluronic acid, collagen, sugars or polysaccharides, and so forth.

Microparticles or nanoparticles, with a therapeutic agent, may be prepared by any techniques known and used in the art. Such techniques include, but are not limited to; single and double emulsion solvent evaporation, spray drying, solvent removal, phase separation, simple and complex coacervation, and interfacial polymerization. Suitable techniques for preparing microparticles or nanoparticles, with a therapeutic agent are disclosed, for example, in Remington: The Science and Practice of Pharmacy, 21st edition, Lippincott Williams & Wilkins (2005) and U.S. Pat. Nos. 6,479,065, 6,998,074, 7,381,716, and 7,332,351.

By way of non limiting example, microspheres may be produced by extrusion-spheroidization, where the active therapeutic ingredient and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, extrudate of substantially uniform shape and size. The shaped extrudate may then be fed onto a rotating disk, which may be smooth or may contain a grid (waffled, grooved, etc.) where the shaped extrudate is broken into smaller pieces, which in time may be worn into a rounded or substantially spherically shaped microspheres. The microspheres may then be dried to a desired residual moisture content and sized by sieving.

In other embodiments, the pore creating material may comprise a liposome. Generally, liposomes comprise an enclosed lipid droplet having a core, typically an aqueous core, containing a compound, such as a therapeutic agent. The therapeutic agent may be chemically conjugated to a lipid component of the liposome. Alternatively, the therapeutic agent may be simply contained within the aqueous compartment inside the liposome or, for hydrophobic therapeutic agents, within the lipid layer of the liposome. Lipososmes are commercially available from a variety of suppliers or may be prepared according to known methods, such as the methods described, for example, in U.S. Pat. Nos. 6,855,296 and 6,984,397. In preferred embodiments, liposomes are shaped as microspheres with a diameter between about 50 microns to 400 microns, between about 100 microns to about 300 microns, or between about 100 microns to about 200 microns.

In yet other embodiments, the pore creating material may comprise microbubbles. Microbubbles may be formed in vitro and mixed with the hydrophilic polymer or may be created in vivo. By way of non-limiting example, to prepare microbubbles in vitro, a vial containing a surfactant solution and gas in the headspace of the vial may be sonicated with a low power ultrasound. Once the sonication is accomplished, the microbubble solution may be withdrawn from the vial and mixed with the biologically absorbable hydrophilic polymer, where disintegration of the microbubbles creates pores in the hydrophilic polymer and releases any therapeutic agent contained therein into the wound site. For example, BMP-2, or any other therapeutic agent, may be added to the surfactant solution prior to sonication.

For the purposes of the instant disclosure, the term "therapeutic agent" means an agent that promotes, induces, increases, or accelerates wound healing or initiates, accelerates or improves tissue growth, decreases or prevents growth undesirable bacteria or fungi, or reduces or eliminates the sensation of pain in the patient. Suitable therapeutic agents include, but are not limited to, antibiotics such as tetracyclines (e.g., minocycline), rifamycins (e.g., rifampin), macrolides (e.g., erythromycin), penicillins (e.g., nafcillin), cephalosporins (e.g., cefazolin), other beta-lactam antibiotics (e.g., imipenem, aztreonam), aminoglycosides (e.g., gentamicin), chloramphenicol, sufonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole) and beta-lactam inhibitors (e.g., sulbactam); analgesics such as Acetaminophen, Aspirin, Clonidine, Flurbiprofen, Indoprofen, Naproxol, Pentazocine, Proxazole, Tramadol, Verilopam, Volazocine, Xylazine, Zucapsaicin, phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, morphine, heroin, hydromorphone, metopon, oxymorphone, levorphanol, codeine, hydrocodone, oxycodone, nalorphine, naloxone, naltrexone, salycilates, phenylbutazone, indomethacin, and phenacetin; anti-cytokines; cytokines; anti-interleukin-1 components (anti-IL-1); anti-TNF alpha; stem cells, including autogenic or allogeninc mesenchymal stem cells, bone marrow aspirate, and/or adipose tissue-derived stromal cells; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Fibroblast Growth Factors (FGFs); Platelet Derived Growth Factors (PDGFs), including PDGF-A, PDGF-B, PDGF-C, and PDGF-D; Growth Differentiation Factors, including rhGDF-5; insulin-related growth factor-I (IGF-I); insulin-related growth factor-II (IGF-II); fibroblast growth factor (FGF) and beta-2-microglobulin (BDGF II), Bone Morphogenetic Proteins (BMPs), including BMP-2 and BMP-7; Transforming Growth Factor betas (TGF-$\beta$s), including TGF-$\beta$-1, TGF-$\beta$-2, and TGF-$\beta$-3; Nell-1 protein, LIM mineralization protein and peptides (see U.S. Patent Publication 2005/0196387); matrix metalloproteinases (MMP) inhibitors; and combinations thereof. For example, the tissue sealant may include microspheres containing rifampin, erythromycin, and BMP-2.

Exemplary MMP inhibitors include, but are not limited to, TIMP-1 and TIMP-2. Certain MMP inhibitors are also described in U.S. Patent Publication 2004/0228853.

The therapeutic agent may be incorporated into the pore creating material, and it may be released from the pore creating material as the pore creating material is being removed and/or by diffusion. The therapeutic agent is preferably administered over a period of between about 24 hours and about 12 weeks, between about 24 hours and about 8 weeks, and between about 24 hours and about 6 weeks.

The instant compositions may also include optional physiologically acceptable carriers, excipients or stabilizers, in the form of lyophilized formulations or aqueous solutions. Methods for preparing therapeutic formulations are known and are disclosed, for example, in Remington: The Science and Practice of Pharmacy, 21st edition, Lippincott Williams & Wilkins (2005).

In yet another exemplary embodiment, the invention provides a method for treating a wound. The method comprising applying a hydrophilic polymer and/or monomers thereof, a cross-linking agent and a pore creating material, which may optionally have a therapeutic agent therein, under conditions that result in cross-linking of the hydrophilic polymer and/or monomers to produce a hydrogel in vivo having the pore creating material scattered throughout it. When the pore creating material comprises a therapeutic agent, the composition is able to administer to a patient a therapeutically effective amount of the therapeutic agent, as well as, induce cells to colonize the hydrogel. Polymer chemistry and hydrogel systems. E. H. Schacht; *Journal of Physics*: Conference Series 3, 22-28 (2004) (3rd Internat. Conference on Radiotherapy Gel Dosimetry); Preparation of Wound Dressing Using Hydrogel Polyurethane Foam. Jae-Suk Lee et al. *Trends Biomater. Artif Organs* 15(1):4-6 (2001); U.S. Patent Pub. 2006/0051427; U.S. Pat. No. 7,063,748.

In an exemplary embodiment, the hydrophilic polymer is polymerized or cross-linked without using irradiation.

The term "therapeutically effective amount" means a quantity of a therapeutic agent which, when administered to a patient or subject, is sufficient to result in an improvement in patient's condition. The improvement maybe determined in a variety of ways. Additionally, the improvement does not mean a cure and may include only a marginal change in the patient's condition.

While the invention has been described in detail in the foregoing description, the same is to be considered as illustrative and not restrictive in character, it being understood that only the preferred embodiment has been shown and described and that all changes and modifications that come within the spirit of the invention are desired to be protected. In addition, all publications, including Patents and Patent Applications, cited herein are hereby incorporated by reference in their entirety.

What is claimed is:

1. A method of treating an internal wound, the method comprising: applying a biologically absorbable hydrophilic polymer to the internal wound, the internal wound comprising a surgical incision in a spinal disc, the biologically absorbable hydrophilic polymer comprising a pore creating material dispersed throughout it and containing a therapeutic agent, wherein the biologically absorbable hydrophilic polymer adheres to the internal wound, and the pore creating material comprises liposomes that are not cross-linked; cross-linking the hydrophilic polymer in situ via free radical polymerization that is redox initiated to seal the internal wound in a subject by applying a chemical crosslinking agent to the hydrophilic polymer; and allowing the pore creating material to absorb or degrade faster than the cross-linked hydrophilic polymer so as to release the therapeutic compound and create pores in the cross-linked hydrophilic polymer by the absorption or degradation of the pore creating material in vivo, thereby facilitating cellular colonization of the cross-linked hydrophilic polymer in situ through the pores of the cross-linked hydrophilic polymer, and an initial ratio of the biologically absorbable hydrophilic polymer to the pore creating material is between about 25% and about 75% v/v, and the hydrophilic polymer does not comprise gelatin, and the cross-linking of the biologically absorbable hydrophilic polymer in situ is done in less than about 5 minutes, and the cross-linked hydrophilic polymer has a burst strength of at least about 3 psi.

2. The method of treating an internal wound according to claim 1, wherein cross-linking of the hydrophilic polymer results in swelling of less than about 10% by volume.

3. The method of treating an internal wound according to claim 1, wherein the cross-linked hydrophilic polymer has a residence time in the subject of at least about 4 weeks before being fully absorbed or degraded.

4. The method of treating an internal wound according to claim 1, further comprising forming a liquid barrier covering the wound.

5. The method of treating an internal wound according to claim 1, wherein cross-linking the hydrophilic polymer in situ is done in less than about 1 minute.

6. The method of treating an internal wound according to claim 1, wherein the pore creating material is a ceramic and is absorbed or degraded in less than about 168 hours.

7. The method of treating an internal wound according to claim 1, wherein the pore creating material is absorbed or degraded in less than about 48 hours.

8. The method of treating an internal wound according to claim 1, wherein the therapeutic agent is selected from the group consisting of cytokines, anti-IL-1, anti-TNF alpha, mesenchymal stem cells, bone marrow aspirate, adipose tissue-derived stromal cells, Vascular Endothelial Growth Factors (VEGFs), Connective Tissue Growth Factors (CTGFs), Fibroblast Growth Factors (FGFs), Platelet Derived Growth Factors (PDGFs), Growth Differentiation Factors, insulin-related growth factor-I (IGF-I), insulin-related growth factor-II (IGF-II); fibroblast growth factor (FGF), beta-2-microglobulin (BDGF II), Bone Morphogenetic Proteins (BMPs), Transforming Growth Factor betas (TGF-βs), Nell-1 protein, LIM mineralization protein, matrix metalloproteinases (MMP) inhibitors and combinations thereof.

9. The method of treating an internal wound according to claim 1, wherein the therapeutic agent is an antimicrobial agent.

10. The method of treating an internal wound according to claim 1, wherein the therapeutic agent is selected from the group consisting of BMP-2, BMP-7, BMP-12, GDF-5 and combinations thereof.

11. The method of treating an internal wound according to claim 1, wherein the cross-linked hydrophilic polymer has a viscosity from about 25 cP to about 300 cP.

12. The method of treating an internal wound according to claim 1, wherein the pores have a pore size of between about 100 μm and about 400 μm.

13. The method of treating an internal wound according to claim 1, wherein the biologically absorbable hydrophilic polymer comprises polyisobutylene, polyisoprene, neoprene, nitrile N-vinyl pyrrolidone, N-vinyl lactams, acrylamide, polyurethanes and polyacrylonitrile, or glycosaminoglycans.

* * * * *